(12) United States Patent
Schanke et al.

(10) Patent No.: US 6,211,255 B1
(45) Date of Patent: Apr. 3, 2001

(54) FISCHER-TROPSCH SYNTHESIS

(75) Inventors: Dag Schanke; Edvard Bergene; Anders Holmen, all of Trondheim (NO)

(73) Assignee: Den Norske Stats Oljeselskap A.S., Stavanger (NO)

( * ) Notice: Subject to any disclaimer, the term of this patent is extended or adjusted under 35 U.S.C. 154(b) by 0 days.

(21) Appl. No.: 09/380,134

(22) PCT Filed: Feb. 27, 1998

(86) PCT No.: PCT/NO98/00065

§ 371 Date: Nov. 23, 1999

§ 102(e) Date: Nov. 23, 1999

(87) PCT Pub. No.: WO98/38147

PCT Pub. Date: Sep. 3, 1998

(30) Foreign Application Priority Data

Feb. 28, 1997 (GB) .................................................. 9704217

(51) Int. Cl.$^7$ ......................... C07C 27/00; B01D 50/00; B01J 35/02
(52) U.S. Cl. ............................................................ 518/715
(58) Field of Search ................................... 518/700, 715; 422/180, 211

(56) References Cited

U.S. PATENT DOCUMENTS 4,422,961  12/1983  Gray .
5,023,276 * 6/1991 Yarrington et al. ................... 514/703
5,461,022  10/1995  Dosch et al. .

FOREIGN PATENT DOCUMENTS

WO 90/07377   7/1990  (WO) .

OTHER PUBLICATIONS

Andrzej Cybulski et al., "Monoliths in Heterogeneous Catalysis", 1994, pp. 179–193 and 200–201, Marcel Dekker, Inc.

* cited by examiner

Primary Examiner—Johann Richter
Assistant Examiner—J. Parsa
(74) Attorney, Agent, or Firm—Kirkpatrick & Lockhart LLP

(57) ABSTRACT

The present invention provides a reaction system for a Fischer-Tropsch synthesis which has high mass transfer characteristics at the catalyst. The reactor comprises a monolithic catalyst comprising a solid body defining discrete and continuous channels extending from one end of the body to the other. The walls of the channels contain a conventional Fischer-Tropsch catalyst; conventional promoters may also be included. The body preferably may also comprises channels for conducting coolants which are arranged traversely to the reaction channels.

25 Claims, 5 Drawing Sheets

SBCR = SLURRY BUBBLE COLUMN REACTOR
 (SOLID FRACTION = 0.15 (VOL), $u_g$ = 16 cm/s
MR = MONOLITH REACTOR
 (SOLID FRACTION = 0.15 (VOL), $u_g$ = 16 cm/s, $k = k_{SBCR}$)
MTFBR = MULTITUBULAR FIXED-BED REACTOR
 (SOLID FRACTION = 0.6 (VOL), $u_g$ = 50 cm/s $k = k_{SBCR}/3$).

FISCHER-TROPSCH SYNTHESIS

This application is a 371 of PCT/No. 98/00065 filed on Feb. 27, 1998.

The present invention relates to a Fischer-Tropsch synthesis.

Conventional methods of operating a low temperature Fischer-Tropsch synthesis employ fixed bed reactors. The catalytically active material is generally carried on relatively large carrier particles and this results in poor intraparticle mass transfer characteristics. Also, the catalyst particles are packed in the tubes of a shell and tube arrangement with coolant on the shell side. This means that the space/time yield is limited by the heat transfer in the catalyst bed.

An alternative is to operate the fixed bed as a trickle-bed reactor. This may have advantages from the point of view of heat transfer, however, the poor intraparticle mass transfer characteristics remain.

It has also been proposed to carry out an F-T synthesis in a slurry bubble column reactor. Here, the catalyst particles would be significantly smaller since they would be in suspension in the liquid product. This in turn gives rise to significantly improved mass transfer characteristics within the catalyst particles. However, this type of reaction system can be disadvantageous in that separation of the catalyst from the product can be troublesome. There is also back mixing, due to the nature of the reactor, which is less efficient in terms of reactor volume than a plug flow reactor.

It is an object of the present invention to provide a reaction system for an F-T synthesis which has high mass transfer characteristics at the catalyst and in which heat transfer is not a significantly limiting factor, without the drawback of a difficult catalyst separation.

As world oil resources diminish, natural gas is becoming more attractive as an energy source and methods of upgrading this to higher hydrocarbon fuels are increasing in importance. Thus, in one system, the methane (natural gas) is reformed to CO and $H_2$ and this synthesis gas is subjected to a Fischer-Tropsch reaction to form higher hydrocarbon products.

Gas fields are now being discovered at significant distances offshore and under certain circumstances it is not commercially viable to pipe the gas on-shore for processing. It would be advantageous, therefore, if the natural gas in these remote fields could be processed on board marine vessels at the fields and then taken to port by those vessels or by other transport vessels. Under these conditions, reactor size is crucial, and the existing fixed bed and slurry reactors are undesirably large. They are also sensitive to movement, particularly the slurry reactor which would be unstable in heavy seas.

It is therefore a further object of the invention to provide a reaction system for an F-T synthesis in which the reactor size is minimised and which is less sensitive to movement than existing systems.

Accordingly, the invention is directed to the use of a monolithic catalyst to conduct a Fischer-Tropsch synthesis, in which the monolith comprises a solid body defining a series of discrete and continuous channels extending from one end of the body to the other, the walls of the channels consisting of or containing a Fischer-Tropsch catalyst.

The invention also provides a method of conducting a Fischer-Tropsch synthesis reaction which comprises: passing synthesis gas comprising $H_2$ and CO through discrete and continuous channels in a monolithic catalyst, the walls of the channels consisting of or containing a Fischer-Tropsch catalyst; removing the liquid product from the monolith; and removing heat produced in the reaction in the liquid product.

Preferably heat from the reaction is removed from the liquid product stream outside the reactor and a portion of the liquid product stream is recycled to the reactor. Unreacted synthesis gas may be recycled from the reactor, for example to the synthesis gas production unit.

Preferably, the synthesis gas feed and the liquid product flow co-currently. Preferably the synthesis gas feed and liquid product travel along the channels in a slug flow or Taylor Flow regime. Taylor Flow of a gas and liquid in a channel is defined as periodic cylindrical gas bubbles in the liquid having almost the same diameter as the channel and without entrained gas bubbles between successive cylindrical bubbles. Preferably, the flow is downwards.

Alternatively, the gas/liquid flows could be counter-current.

In a preferred form, the invention provides a reaction system for a Fischer-Tropsch synthesis which comprises a reactor including a monolithic catalyst and having an inlet for synthesis gas comprising $H_2$ and CO and an outlet for liquid product, the monolithic catalyst comprising a solid body defining a series of discrete and continuous channels extending from one end of the body to the other, the walls of the channels consisting of or containing a Fischer-Tropsch catalyst, whereby the synthesis gas is supplied via the inlet and is passed through the channels where the synthesis takes place and liquid product is removed via the outlet, the heat produced by the reaction being removed from the system by the liquid product.

Mass transfer (diffusion) effects are also very important in determining selectivity. Diffusion rates in the liquid phase are typically 3 orders of magnitude slower than in the gas phase, meaning that even slow reactions may be diffusion limited in liquid phase. Recent investigations have shown that a moderate diffusion resistance within the catalyst pellet (intraparticle) can give a strong negative influence on C5+ selectivity. The key parameter is the characteristic diffusion distance, determined by the catalyst pellet size or the thickness of a catalytic layer. As a guideline, negative effects on selectivity are experienced for diffusion lengths above 0.1–0.4 mm, corresponding to 0.2–0.8 mm diameter spherical pellets (the exact value depending on catalyst properties and reaction conditions).

Conventional fixed bed reactors typically use 2–6 mm diameter pellets in order to avoid an unacceptable pressure drop through the catalyst bed. In a fixed bed reactor, the selectivity problem can be solved by using catalyst pellets where the catalytic material is deposited in a thin outer layer ("egg-shell" catalysts). However, this means that only a fraction of the catalyst present in the reactor is participating in the reaction, reducing the solid fraction from typically 60% to about 23% for a 2 mm diameter spherical particle with a 0.15 mm catalytic layer. In a slurry reactor, the selectivity problem is solved by using small catalyst particles, usually 0.1 mm or less.

In the proposed monolith reactor concept, a short diffusion distance (typically <0.15 mm) can be maintained without having to reduce the fraction of active material, as a result of the fact that the catalyst is located in the thin walls of the monolith structure.

The Fischer-Tropsch synthesis is a strongly exothermal reaction and effective heat transfer is a prerequisite for successful reactor operation. In a fixed bed reactor, the catalyst is located within tubes and the heat is removed by steam generation on the shell side. The space time yields are therefore limited by the heat transfer properties of the reactor. In addition, the maximum conversion per pass is limited by the high gas velocities necessary for achieving optimum heat transfer. The heat transfer properties can be improved by decreasing the tube diameter, but this increases the pressure drop. In addition, the cost and weight of the reactor will increase strongly with decreasing tube diameter. In practice, significant axial and radial temperature gradients are unavoidable in fixed bed reactors used for FT-synthesis.

In slurry reactors, the catalyst/slurry is located on the shell side and the heat of reaction is removed by steam generation on the tube side. Due to the turbulent motion of the slurry, the heat transfer properties are more favourable and the necessary heat transfer area is drastically reduced when compared to a fixed bed reactor.

In the proposed monolith reactor design, cooling is performed by direct heat removal by the production stream (preferably the heavy FT products) which may circulate. The circulating liquid can then be cooled in an external heat exchanger. If necessary, the cooling can be carried out in stages by dividing the reactor in different sections with separate cooling circuits.

In slurry reactors, the productivity of the reactor (space time yield) may be limited by the gas-liquid mass transfer, i.e. from gas bubbles to the liquid. The characteristic mass-transfer area is therefore the gas-liquid interfacial area, which is roughly an order of magnitude smaller than the external catalyst area.

In a monolithic reactor operating in two-phase flow (gas+liquid), particularly under Taylor Flow conditions, mass transfer occurs mainly in the thin film between the cylindrical bubbles and the channel walls containing the catalytic material. This mode of flow occurs over a wide range of gas and liquid superficial velocities. However, at very high gas velocities, the flow regime changes to "annular flow", characterized by less favorable mass transfer properties.

The high gas-liquid mass transfer rates (compared to trickle-bed reactors or slurry reactors) and the high liquid velocities possible (compared to trickle-bed reactors) are factors that make the monolith type of reactor well suited for FT-synthesis.

Another desirable property of monolith reactors is the extremely low pressure drop for liquids and gases over the catalyst bed, which is 1–2 orders of magnitude lower than in a packed bed (trickle-bed or gas-phase fixed-bed) reactor. This is an important factor at high gas and liquid superficial velocities and in cases where reactants or liquid are recycled to the reactor. The problem of uneven gas or liquid distribution, bypassing etc. is also much smaller than in packed-bed reactors.

A primary goal in any FT-process is to achieve a high conversion per pass, in order to achieve high yields and reduce recycle and investment costs. For any reaction, the reaction kinetics and the mixing characteristics of the reactor will determine the necessary reaction volume for reaching the desired conversion. For a given feedrate to the reactor, an increase in conversion is achieved by increasing the height of the reactor.

A slurry reactor is characterized by extensive backmixing, resulting in relatively flat concentration profiles for reactants and products. As an approximation, the reactor can be assumed to operate as a perfectly mixed reactor.

On the other hand, tubular fixed-bed reactors and a monolith reactor will show negligible backmixing, i.e. near plug-flow. The narrow channels of a monolith and the Taylor-flow mode of operation in two-phase flow results in almost perfect plug-flow. Scale-up is therefore simple since the entire reactor can be described by a single channel.

Classical chemical reaction engineering principles teach that chemical reactions characterized by a positive order dependence of reactant concentrations are most efficiently carried out in plug-flow. In other words, the necessary reaction (or catalyst) volume (i.e. the reactor height) is smaller for a reactor operating in plug-flow, compared to mixed flow. The disadvantage of mixed-flow reactors increase with increasing conversion and increasing reaction order.

If the FT-synthesis is assumed to have a 1. order dependency on hydrogen partial pressure, the necessary volume for a perfectly mixed reactor will be approximately 3 times larger than in a plug-flow reactor at 90% conversion and the same catalyst concentration, temperature and pressure. However, 1. order kinetics is not an accurate representation of the FT-reaction. The apparent pressure order is less than 1.0, and the kinetics can for the present purpose be approximated by a power function:

$$r = k\, p_{H2}^{+0.5} p_{CO}^{-0.1}$$

r=CO consumption rate
k=rate constant
$p_{H2}$, $p_{CO}$=partial pressure of $H_2$ and CO, respectively A comparison of the performance of various FT-reactors is shown in FIG. 9. The monolith and slurry reactors have been assumed to have the same catalyst concentration per volume of reactor and a typical inlet gas velocity $u_g$=16 cm/s. The fixed-bed reactor, due to the less favourable heat transfer properties, has been assumed to operate at ⅓ of the rates achievable in the SBCR or MR cases, either as a result of lower catalyst activity, lower temperatures or both. It is well known from FT and methanol synthesis that multi-tube fixed bed reactors must operate at high gas velocities in order to obtain optimum heat transfer. 50 cm/s has been chosen as a representative value for the fixed bed reactor. The reaction rates and inlet velocities are representative values for the reactors considered.

It is evident from FIG. 9 that the difference in reactor height for the SBCR and MR is relatively small for low-moderate conversions (up to about 60%). However, for conversions above 80% and in particular above 90%, the difference in reactor height becomes significant. For the fixed bed reactor, the high linear velocity makes it virtually impossible to achieve high single pass conversions.

Thus, the monolith can achieve higher conversions than a backmixed slurry reactor, and is of particular interest for cases where extremely high conversions are desired (>90%).

As mentioned above, a slurry reactor needs continuous catalyst/product separation in order to operate successfully and for producing a catalyst-free product. Such arrangements are not necessary in a monolith reactor. Heavy products are easily removed from the liquid recycle stream as required for maintaining a constant inventory of liquid.

In many monolith applications, the thermal stability of the material and the ability to withstand rapid temperature variations are both of great importance. Therefore, the channel structure of a monolith usually consists of a low-surface area ceramic material. The surface area can be increased by depositing a high-surface area material (like γ-$Al_2O_3$), e.g. by the so-called washcoating technique. Catalytically active materials can then be incorporated into the washcoat by known techniques, like impregnation, precipitation, ion-exchange, vapour deposition etc. Alternatively, the low surface area base material can be washcoated with the catalytic material itself.

Thus in one preferred form, the monolithic catalyst comprises an inactive substrate with a relatively low specific surface area, and, lining the channels, a relatively high specific area catalyst support impregnated with a catalytically active material. Preferably the catalyst support material and the active material are deposited simultaneously on the walls of the channels. Alternatively, the catalyst support material is first deposited on the walls of the channels and is subsequently impregnated with the active material. The inactive substrate may be a ceramic material or a metal. Examples of suitable materials are set out in Table 1 (taken from "Monolithic Catalysts for Nonautomobile Applications" by S Irandoust and B Andersson, Catal. Rev. Sci. Eng., 30(3), 1988).

TABLE 1

Materials for Monolithic Substrates

| Name | Composition |
|---|---|
| α- and γ-Alumina | $Al_2O_3$ |
| Cordierite | $2MgO.2Al_2O_3.5SiO_2$ |
| Cordierite-mullite | $2MgO.2Al_2O_3.5SiO_2$—$2Al_2O_3.2SiO_2$ |
| Magnesium aluminate-spinel | $MgO$—$MgO.Al_2O_3$ |
| Mullite | $3Al_2O_3.SiO_2$ |
| Mullite-aluminum titanate | $3Al_2O_3.2SiO_2$—$Al_2O_3.TiO_2$ |
| Silica | $SiO_2$ |
| Silicon carbide | $SiC$ |
| Silicon nitride | $Si_3N_4$ |
| Spinel | $MgO.Al_2O_3$ |
| Titania | $TiO_2$ |
| Zeolites | $Al_2O_3$—$SiO_2$ |
| Zirconia | $ZrO_2$ |
| Zirconia-spinel | $ZrO_2$—$MgO.Al_2O_3$ |
| Metallic | Fe—Cr—Al—Yt |

A monolith-based FT catalyst can thus be made by impregnation (or by other techniques) of an active FT-metal (Co,Fe,Ru,Ni) and suitable promoters on a high-surface area washcoated monolith or by washcoating the finished FT-catalyst onto the low-surface area monolith.

In slower reactions like the Fischer-Tropsch synthesis, thermal stability is not a critical factor. In such cases, monoliths can be made directly from high surface area materials, for example gamma-$Al_2O_3$, $SiO_2$, $TiO_2$ or zeolites. The catalytic material (e.g. cobalt, iron ruthenium or nickel in the case of FT-synthesis) and optionally suitable promoters can then be incorporated into the total volume of the monolith (by any of the known techniques), thus increasing the catalyst loading of the reactor compared to the washcoat method. Alternatively, the monolith can be produced directly from the FT-catalyst. Production of high surface area monoliths is usually achieved by extrusion.

Thus, in another preferred form, the monolithic catalyst comprises an inactive substrate with a relatively high specific surface area in which the walls of the channels are impregnated with a catalytically active material. In an alternative form, the monolithic catalyst comprises an extrusion of a relatively high specific surface area material incorporating a catalytically active material. Preferably, the high specific surface area material is γ-$Al_2O_3$, $SiO_2$, $TiO_2$ or zeolite. Generally suitable materials also include transition aluminas, alumina/silica, magnesium aluminate spinel and titania/silica, or any high surface area ceramic material.

The particular F-T active catalyst material selected will depend to an extent on the final product required, however, preferred materials include Co, Fe, Ru and/or Ni. The catalyst may include a promoter. Suitable promoters include Re, Pt, Ir, Rh, Pd and Ru.

The monolith preferably has an open area or void fraction of 50 to 90%, more preferably 60–80%, for example 70. It may have a cell density of 100 to 1000 cells/in$^2$ (15.5 to 155 cells/cm$^2$), preferably 200 to 600 cells/in$^2$ (31.0 to 93.0 cells/cm$^2$), most preferably 300–500. The wall thickness is preferably 0.05 to 0.4 mm, more preferably 0.1–0.3, for example 0.15.

The monolith, which may be extruded, may have a length in the centimeters to meters range, the ultimate maximum length being limited only by manufacturing techniques. A reactor of the required size can be produced by stacking together monolithic catalyst blocks.

The invention also extends to a monolithic catalyst per se, as described, for carrying out an F-T synthesis.

The monolithic catalyst reactor system described exhibits in particular the following qualities, many of which represent significant advantages over known F-T reactor systems:
a) Plug-flow, very high conversions possible or short reactors for moderate–high conversions
b) Simple scale-up
c) Short diffusion distance in monolith walls, good selectivity
d) High gas-liquid mass-transfer rates in two-phase flow
e) High liquid and gas throughputs possible
f) Low pressure drop
g) Temperature control by direct cooling of catalyst with liquid medium and external heat removal
h) No wax-catalyst separation necessary The invention may be carried into practice in various ways and some embodiments will now be described by way of example with reference to FIGS. 1 to 8 of the accompanying drawings.

BRIEF DESCRIPTION OF THE DRAWINGS

FIG. 4a is an end view of the monolithic catalyst;

FIG. 4b is an enlarged view of part of FIG. 4a;

FIG. 1 shows a reaction system for an F-T synthesis embodying the present invention. The system comprises a reactor 11 containing a monolithic catalyst 12 and a liquid distributor 13 above the catalyst monolith 12. The reactor 11 also has a gas inlet 14 near the top, a liquid outlet 15 at the base and a gas outlet 16 near the base. The liquid outlet 15 is joined to the liquid distributor via a recycle stream 17 which includes a pump 18 and a heat exchanger 19. The recycle stream 17 has a liquid product outlet 21.

Figure 1:
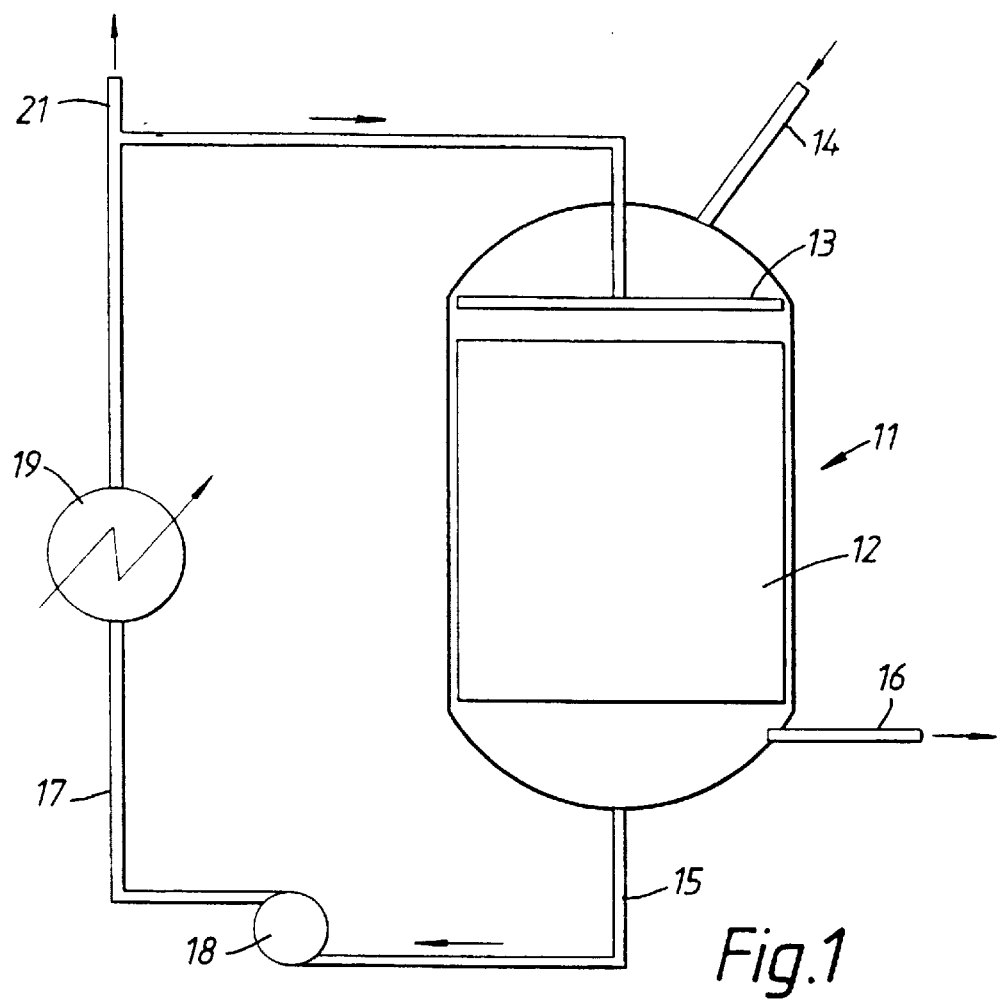
FIG. 1 is a schematic diagram of a reaction system according to the invention.

In use, synthesis gas ($H_2$ and CO) is introduced via the gas inlet 14 and product liquid recycled to the distributor 13. The liquid and gas are drawn down through longitudinal channels in the monolith 12 under a Taylor flow regime. The gases react to form hydrocarbons, with a preference for hydrocarbons with 5 or more carbon atoms. The liquid product is withdrawn via the outlet 15 by means of the pump 18 and is cooled in the heat exchanger 19 where water is heated and vaporized. A portion is removed at the product outlet 21 and the remainder is recycled to the distributor 13. Any unreacted gas and any gaseous product is removed at the gas outlet 16 and possibly recycled.

Figure 2:
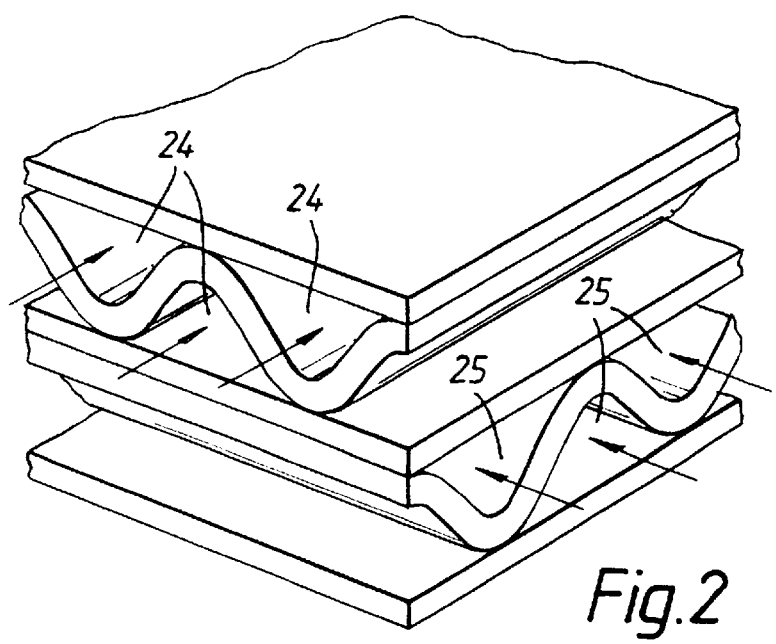
FIG. 2 is a perspective view in part of an alternative arrangement.

In an alternative construction shown in FIG. 2, the monolith is a cross-flow design. In this case, the gases are arranged to travel along one series of channels 24 and the cooling liquid along the transverse channels 25 which alternate vertically with the gas channels.

Figure 3:
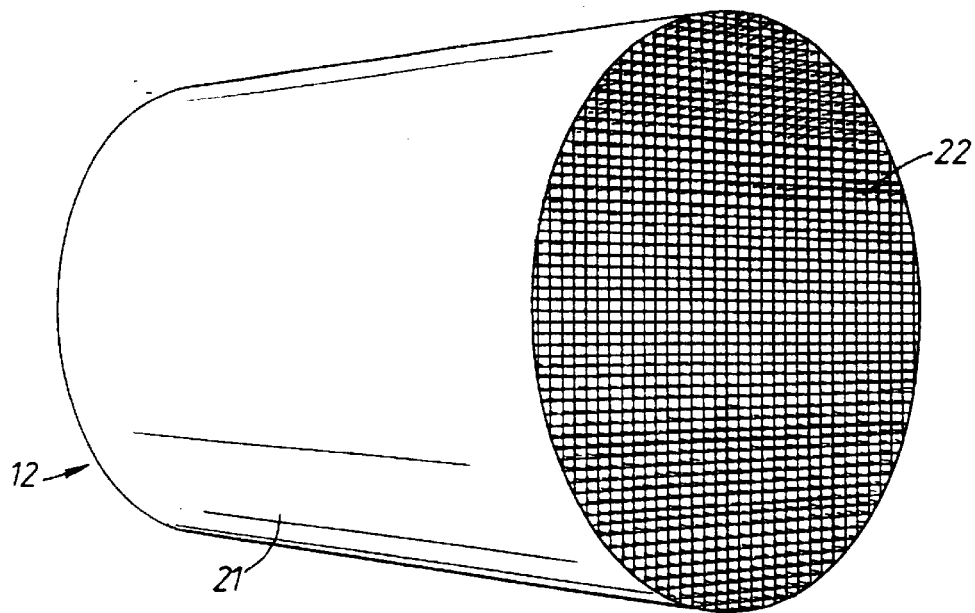
FIG. 3 is an isometric sketch of a monolithic catalyst.
Figures 4A, 4B:
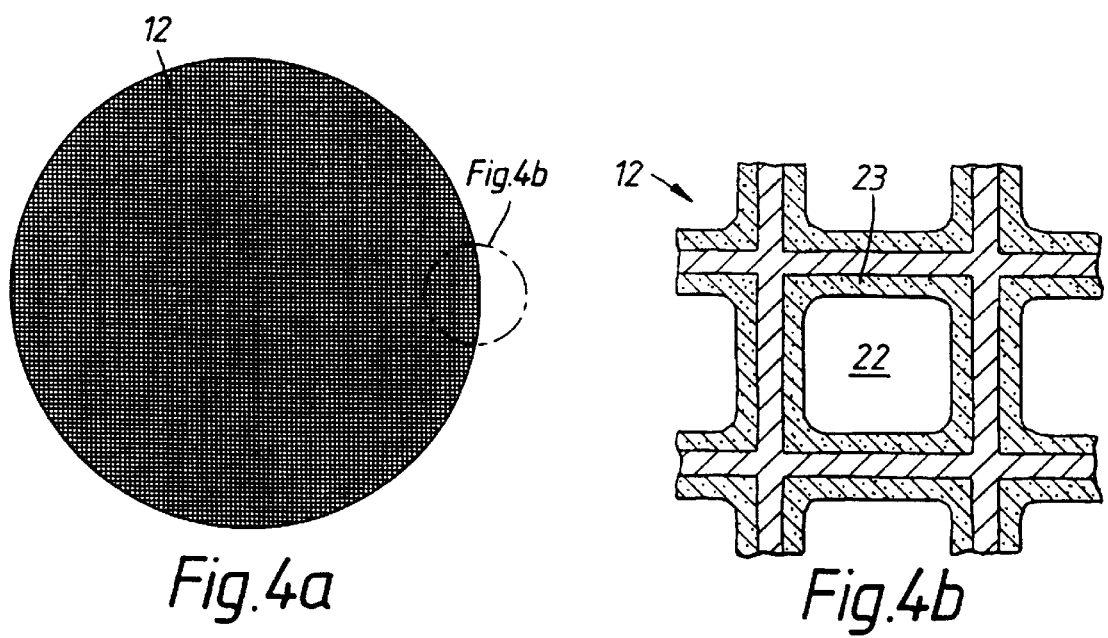

The monolith 12 as shown in FIGS. 3, 4a and 4b is cylindrical, though any suitable shape could be employed such as rectangular. It comprises an outer wall 21, preferably formed of the same material as the monolith body which is formed with regular longitudinal channels 22 of square section though, again, any shape could be employed. The channels 22 are discrete and continuous and extend from one end of the monolith to the other. In this case the monolith 12 is of low surface area cordierite, the surface area being 0.1 to 1.0 m$^2$/g. The walls of the channels 22 have a layer 23 of a high surface area material, such as γ-Al$_2$O$_3$, the surface area being about 200 m$^2$/g. This material is impregnated with an active catalyst material such as Co with a promoter such as Re.

Figure 5A:
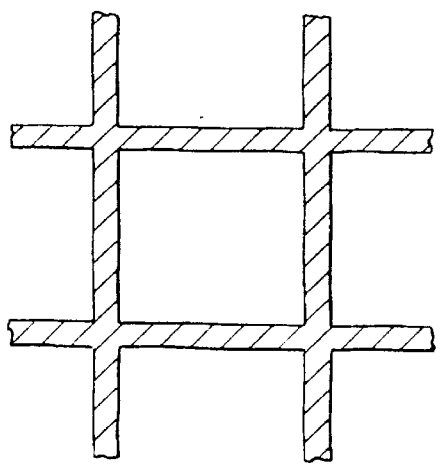
FIGS. 5a to 5c are sequential views, similar to FIG. 4b, in the manufacture of a monolithic catalyst according to a first method.
Figure 5B:
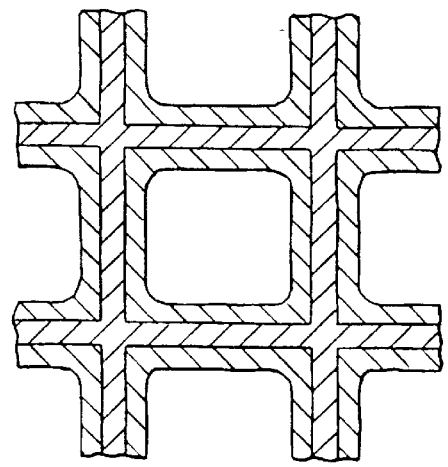
Figure 5C:
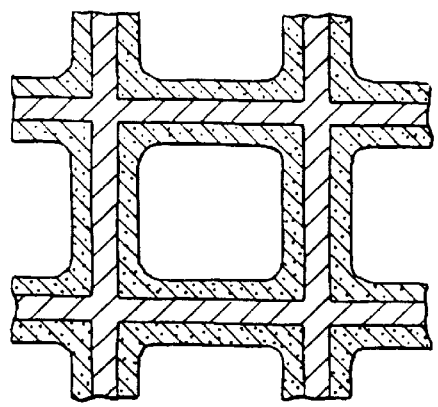

One method of manufacturing the monolith 12 is shown in FIGS. 5a to 5c. A monolithic support is formed from an inactive low surface area (typically 0.1 to 1.0 m$^2$/g) material such as cordierite by mixing fine cordierite powder with plasticizers and binders to form a paste which is then extruded. The extruded body is dried and fired at a high temperature and has a large number of square section channels (FIG. 5a).

Active material is then applied to this monolith support by a washcoating technique. A high surface area (20 to 200 m$^2$/g) material such as γ-alumina may be used. The monolith is dipped into a slurry of the high surface area material and this is then dried and heat treated, leaving a layer of the high surface area material on the walls of the channels (FIG. 5b).

Active material such as Co is introduced into the washcoat by impregnation, precipitation ion exchange from solution or other known methods (FIG. 5c).

Figure 6A:
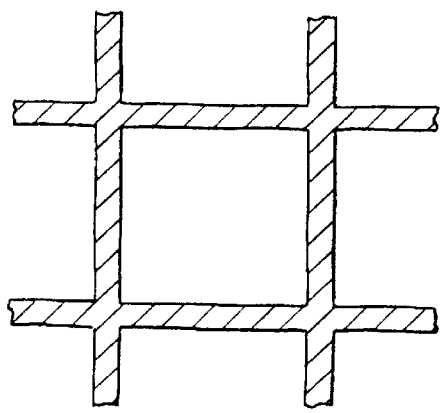
FIGS. 6a and 6b are sequential views showing a second method.
Figure 6B:
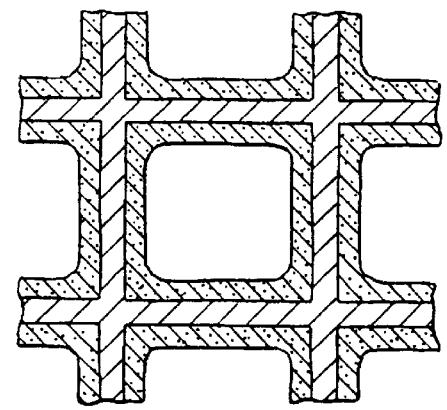

An alternative washcoat method is shown in FIGS. 6a and 6b. In this case the monolith support is prepared in the same way as that shown in FIG. 5a (FIG. 6a). Then, however the monolith is dipped in a liquid suspension containing a fine powder of a Fischer-Tropsch catalyst. Thus when the washcoated layer is dried, it already contains the active material (FIG. 6b).

Figure 7A:
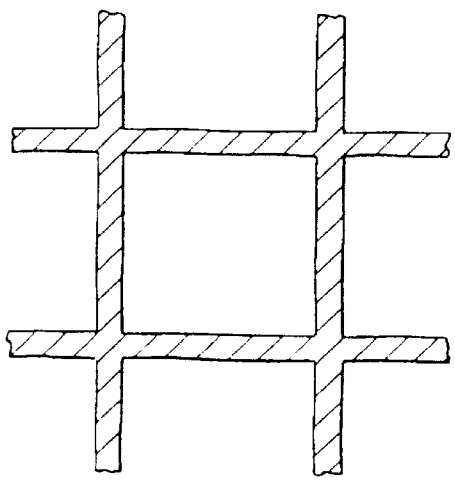
FIGS. 7a and 7b are sequential views showing a third method.
Figure 7B:
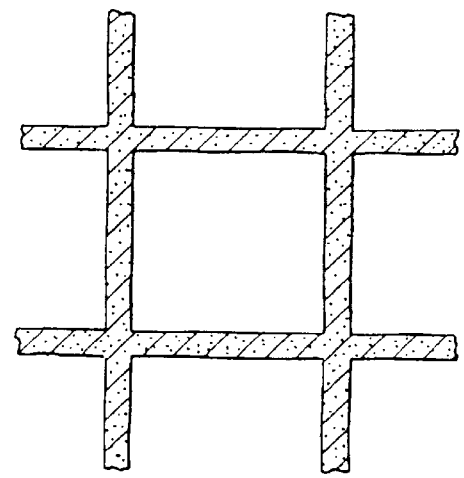

Another method of producing the monolith is shown in FIGS. 7a and 7b. Here, the support material is itself an inactive high surface area material. The monolithic support is therefore formed by extrusion in the same way as described above, but using the high surface area material (FIG. 7a).

The support material is then impregnated with the active material from solution in the same way as the high surface area layer in the washcoating methods (FIG. 7b).

Figure 8A:
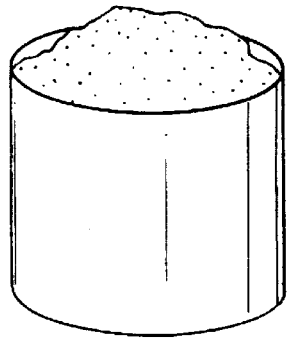
FIGS. 8a and 8b are sequential views showing a fourth method.
Figure 8B:
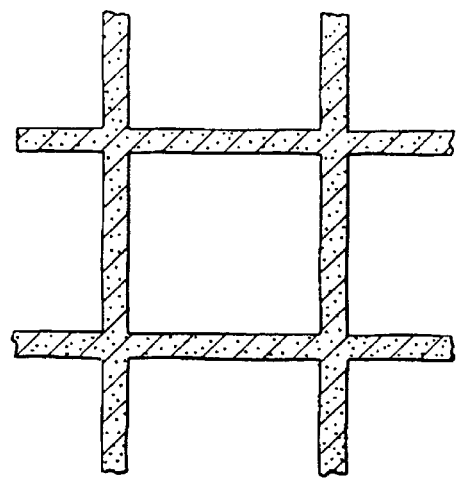
Figure 9:
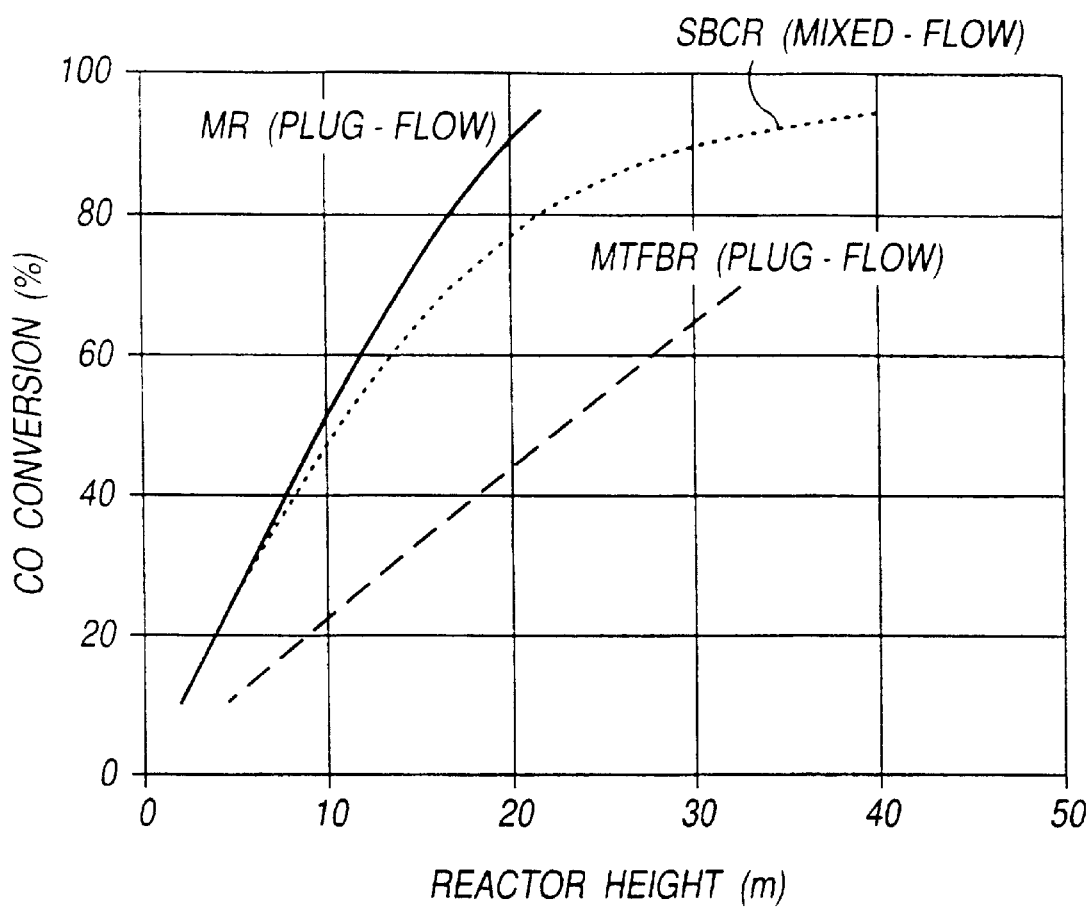
FIG. 9 is a comparison in graph form of the performance of various FT-reactors.

In an alternative direct extrusion method, shown in FIGS. 8a and 8b, a paste of catalyst (i.e. a high surface area support material already containing active material) is extruded, dried and fired to form a high surface area support already containing the active material.

Naturally, to a certain extent, these methods could be combined in order to produce the desired catalyst properties.

The invention will now be further illustrated in the following Examples.

Catalyst Preparation

EXAMPLE 1
Conventional Catalysts 465 g of γ-Al$_2$O$_3$ (Puralox B-5207 from Condea) was sieved to 38–53 μm particles and calcined in air at 500° C. for 10 hours before use. 582 g of Co(NO$_3$)$_2$6H$_2$O and 9.7 g of HReO$_4$ (80–85% solution) was dissolved in deionized water to produce 740 ml of impregnating solution which was mixed with the γ-Al$_2$O$_3$ support. The resulting catalyst was dried in air at 95° C. for 2 days before calcination in air at 300° C. for 16 hours. The calcined catalyst contained 17 wt % Co and 1 wt % Re. A portion of the catalyst was pressed to larger pellets and then crushed and sieved to various particle sizes, namely 53–75 μm (designated catalyst "A"), 75–150 μm (catalyst "B") and 425–850 μm (catalyst "C").

EXAMPLE 2
Washcoated Monolith Catalysts

Another portion of the catalyst described above was wet grinded further in a ball mill and sieved to <38 microns for use in preparing monolithic catalysts. Approximately 10 cm long cylindrical low surface area cordierite monoliths (Celcor (reg. trademark) from Corning) with a diameter of about 0.9 cm were used as base materials. The monoliths had a cell density of 400 cells/in$^2$ (62 cells/cm$^2$) and 76% open area (void fraction). A slurry of the CoRe/Al$_2$O$_3$ catalyst was prepared by mixing 50 g of the <38 micron catalyst with 100 ml of water. The cordierite monolith was then washcoated with the CoRe/Al$_2$O$_3$ catalyst by dipping the monoliths into the catalyst slurry and blowing away excess slurry from the monolith channels gently with an air gun. 2 catalyst samples were produced in this manner, designated "D" and "E" after dipping the monolith 1 and 2 times respectively. In the latter case, the excess slurry was removed and the catalyst was dried between the first and second dip. The monoliths were dried in air at 130° C. for 16 hours before calcination in air at 400° C. for 2 hours. The calcined monolith catalysts "D" and "E" contained 0.3 g and 0.7 g of CoRe/Al$_2$O$_3$ washcoat, respectively.

EXAMPLE 3
High Surface Area Monolith Catalysts

γ-Al$_2$O$_3$ monoliths from Corning (based on Vista Catapal (reg. trademark) alumina from Vista Chemical Company) with a cell density of 400 cells/in$^2$ (62 cells/cm$^2$) and 70% open area was used as a base material. The surface area of the monolith was 145 m$^2$/g and the pore volume was 0.53 cm$^3$/g. Two 10 cm long cylindrical monoliths with 1 cm diameter were used for catalyst preparation. Two identical catalyst samples were produced by dipping the γ-Al$_2$O$_3$ monoliths into a solution containing 100 g of Co(NO$_3$)$_2$6H$_2$O, 1.75 g of HReO$_4$ (80–85% solution) and 50 g of deionized water. After removing the excess solution, the monoliths were dried in air at 95° C. for 16 hours before calcination in air at 400° C. for 12 hours. The calcined catalysts contained 12 wt % Co and 0.6 wt % Re. The first sample (designated "F") was used without modification, while the second sample ("G") was crushed and sieved to 38–150 μm particles.

Catalyst Testing

The catalysts were tested in a 20 cm long 1 cm ID stainless steel fixed-bed reactor closely surrounded by an electrically heated aluminium jacket. The conventional catalysts (powder) were diluted with an inert material (non porous SiC) in a 1:5 weight ratio in order to minimise temperature gradients. The monolithic catalysts were used as prepared. All catalysts were reduced in flowing hydrogen at a space velocity of 5000 cm$^3$ (STP)/(g$_{cat}$.h) at atmospheric pressure at 350° C. for 16 hours (heating rate from ambient temperature: 1 K/min). The space velocity refers to the amount of CoRe/Al$_2$O$_3$ catalyst present in the reactor. After reduction, the catalyst was cooled to 170° C. in flowing H$_2$ and purged with He before increasing the pressure to 13 bar (1.3 MPa) and switching to a feed mixture consisting of synthesis gas ($H_2/CO=2.1$) premixed with 3 mol % $N_2$ as internal standard. The reaction temperature was then slowly increased to the desired temperature (usually 210° C.). On-line samples were taken at regular intervals and analysed for $N_2$, CO, $CO_2$ and $C_1+$ hydrocarbons on a gas chromatograph.

Catalyst Performance

The performance of the catalysts is shown in the Table 2 below. All data are averaged over a period of >10 hours and are representative of stabilized catalysts, i.e. after more than 30 hours on stream.

Catalysts D–F are according to the invention. Catalysts A–C and G are only included for comparison purposes.

It is shown that the washcoated monolith catalysts (D&E) are as active as the conventional (powder) catalysts (A–C). The application of two washcoat layers (cat. E) on the cordierite base does not influence the catalyst performance compared to the single layer monolith (cat. D).

be present for the reactants ($H_2$,CO) in catalyst particles of sufficient size. Due to the difference in the transport properties of $H_2$ and CO, the particle $H_2$/CO-ratio will increase towards the particle centre and cause the loss of C5+ selectivity. Due to the particular reaction kinetics of CO hydrogenation on cobalt catalysts (i.e. the $H_2$ and CO partial pressure dependency of the reaction rate), strong diffusion effects on selectivity are observed before any significant effects are observed on the overall hydrocarbon formation rate. This is in agreement with the data in the Table 2.

Table 2

Catalyst test results. P=13 bar (1.3 MPa), $H_2/CO=2.1$, 3% inerts in feed. The space velocities and reaction rates are based on the weight of active catalyst ($CoRe/Al_2O_3$).

| CATALYST | Temp. (° C.) | GHSV $(h^{-1})$*) | CO conv. (%) | Reaction rate | | Selectivity (%) | | | |
|---|---|---|---|---|---|---|---|---|---|
| | | | | $(g_{HC}/g_{cat}*h)$ | $(g_{HC}/g_{Co}*h)$ | $CH_4$ | $C_2$–$C_4$ | $C_5+$ | $CO_2$ |
| A | 210 | 10.900 | 27.7 | 0.61 | 3.6 | 9.0 | 7.4 | 82.9 | 0.7 |
| (53–75 micron powder) | | | | | | | | | |
| B | 210 | 10.100 | 26.2 | 0.54 | 3.2 | 9.1 | 7.5 | 82.7 | 0.8 |
| (75–150 micron powder) | | | | | | | | | |
| C | 210 | 7.300 | 33.0 | 0.49 | 2.9 | 21.5 | 12.7 | 64.4 | 1.5 |
| (425–850 micron powder) | | | | | | | | | |
| D | 210 | 16.800 | 16.3 | 0.56 | 3.3 | 8.2 | 7.3 | 83.8 | 0.7 |
| (Cordierite base, 0.3 g cat.) | | | | | | | | | |
| E | 210 | 8.400 | 29.1 | 0.50 | 2.9 | 8.9 | 6.5 | 84.0 | 0.6 |
| (Cordierite base, 0.7 g cat.) | | | | | | | | | |
| F | 195 | 4.060 | 27 | 0.22 (0.5)**) | 1.8 (4.0)**) | 7.I | 6.2 | 86.4 | 0.3 |
| (High surf. area monolith) | | | | | | | | | |
| G | 210 | 6.000 | 30 | 0.36 | 2.9 | 8.2 | 7.1 | 84.5 | 0.2 |
| (Crushed high surf. area monolith) | | | | | | | | | |

*)$cm^3$(STP) syngas/$g_{cat}$*h
**)Estimated reaction rate at 210° C. using an activation energy of 100 kJ/mol The high-surface area monolith catalyst (F) contained more cobalt per volume of reactor than the other catalysts and it was found that 195° C. was the maximum acceptable reactor temperature due to heat removal limitations in a gas-phase reactor. These limitations will not be present in a monolith reactor operating with liquid coolant. After correcting for the temperature difference, it is evident that the high-surface area monolith is at least as active per unit mass of cobalt as the conventional (powder) catalysts and also similar to the crushed high-surface area monolith catalyst (G). The high C5+ selectivity indicates that hot-spots were not present during reaction.

Although the small particle conventional catalysts (A&B) show catalyst performances (reaction rates and selectivities) on the same level as the monolith based catalysts, it is known that such particle sizes cannot be used in a commercial fixed-reactor due to an unacceptable pressure drop. Particle sizes >1 mm (>1000 μm) are necessary in commercial fixed-bed reactors. However, the results for the largest particles in the present series of catalysts (425–850 μm, cat. C) show that conventional catalysts of this size produce unacceptably high methane and light gas ($C_2$–$C_4$) selectivities. The $CO_2$ selectivity is also higher than for small particle or monolith-based catalysts. These differences are caused by intraparticle diffusion effects. Under the prevailing conditions, the catalyst pores become filled with liquid hydrocarbon products and large concentration gradients will

What is claimed is:

1. A process for a Fischer-Tropsch synthesis comprising: passing synthesis gas comprising $H_2$ and CO through discrete and continuous channels in a monolithic catalyst, said channels having walls defining surfaces, said surfaces comprising a Fischer-Tropsch catalyst, removing a liquid product from said monolithic catalyst and removing heat produced in said reaction.

2. The process according to claim 1, wherein said monolithic catalyst is housed within a reactor and heat produced in said reaction is removed in said liquid product.

3. The process according to claim 2, wherein heat is removed from said liquid product stream outside said reactor and a portion of said liquid product stream is recycled to said reactor.

4. The process according to claim 1, wherein heat produced in said reaction is removed by cross-current flow of a cooling medium in separate channels through said monolithic catalyst.

5. The process according to claim 1, wherein said synthesis gas feed and said liquid product flow co-currently.

6. The process according to claim 5, wherein said synthesis gas feed and said liquid product travel along said channels in a Taylor Flow regime.

7. The process according to claim 6, wherein said synthesis gas feed and said liquid product flow downwards through the monolith.

8. The process according to claim 1, wherein said synthesis gas feed and said liquid product flow counter-currently.

9. A reaction apparatus for a Fischer-Tropsch synthesis reaction which comprises:
   a reactor including:
      a monolithic catalyst;
      an inlet for a synthesis gas comprising $H_2$ and CO; and
      an outlet for liquid product, said monolithic catalyst comprising a solid body defining a series of discrete and continuous channels extending from one end of said body to another, said channels having walls defining surfaces, said surfaces comprising a Fischer-Tropsch catalyst, whereby said synthesis gas is supplied via said inlet and is passed through said channels where the reaction takes place and a liquid product is removed via said outlet.

10. The reaction apparatus according to claim 9, wherein monolithic catalyst comprises an inactive substrate with a relatively low specific surface area, and, lining said channels, a relatively high specific area catalyst support containing a catalytically active material.

11. The reaction apparatus according to claim 10, wherein said catalyst support material and said active material are deposited simultaneously on said walls of said channels.

12. The reaction apparatus according to claim 10, wherein said catalyst support material is first deposited on said walls of said channels and said active material is subsequently incorporated into said support material.

13. The reaction apparatus according to claim 10, wherein said substrate is a ceramic material or a metal.

14. The reaction apparatus according to claim 13, wherein said ceramic material is alpha-alumina or cordierite.

15. The reaction apparatus according to claim 9, wherein said monolithic catalyst comprises an inactive substrate with a relatively high specific surface area in which said walls of said channels contain a catalytically active material.

16. The reaction apparatus according to claim 9, wherein said monolithic catalyst comprises an extrusion of a relatively high specific surface area material incorporating a catalytically active material.

17. The reaction apparatus according to claim 10, wherein said relatively high specific surface area material is selected from the group consisting of $Al_2O_3$, $SiO_2$, $TiO_2$ and zeolite.

18. The reaction apparatus according to claim 9, wherein said active Fischer-Tropsch catalyst material is selected from the group consisting of CO, Fe, Ru, Ni and combinations thereof.

19. The reaction apparatus according to claim 9, further incorporating a promoter.

20. The reaction apparatus according to claim 19, wherein said promoter is selected from the group consisting of Re, Pt, Ir, Rh, Pd, Ru and combinations thereof.

21. The reaction apparatus according to claim 9, wherein said monolithic catalyst has a void fraction of about 50 to about 90%.

22. The reaction apparatus according to claim 9, wherein said monolithic catalyst has a cell density of about 100 to about 1,000 cell/in$^2$.

23. The reaction apparatus according to claim 9, wherein said monolithic catalyst has a wall thickness of about 0.05 to about 0.4 mm.

24. The reaction apparatus according to as claimed in any one of claims 9 to 23, comprising a plurality of said monolithic catalysts.

25. A process for a Fischer-Tropsch synthesis comprising: passing synthesis gas comprising $H_2$ and CO through discrete and continuous channels in a monolithic catalyst, said channels having walls defining surfaces, said surfaces comprising a Fischer-Tropsch catalyst, removing a liquid product from said monolithic catalyst.

\* \* \* \* \*